US012502154B2

(12) United States Patent
Liu

(10) Patent No.: US 12,502,154 B2
(45) Date of Patent: Dec. 23, 2025

(54) MEDICAL IMAGING METHOD, DEVICE, AND ELECTRONIC APPARATUS

(71) Applicant: SHANGHAI UNITED IMAGING HEALTHCARE CO., LTD., Shanghai (CN)

(72) Inventor: Yang-Yi Liu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 182 days.

(21) Appl. No.: 18/399,794

(22) Filed: Dec. 29, 2023

(65) Prior Publication Data

US 2024/0215939 A1 Jul. 4, 2024

(30) Foreign Application Priority Data

Dec. 30, 2022 (CN) ........................ 202211738761.8

(51) Int. Cl.

*A61B 6/10* (2006.01)
*A61B 6/00* (2006.01)
*A61B 6/42* (2024.01)
*G06T 11/00* (2006.01)

(52) U.S. Cl.

CPC .............. *A61B 6/542* (2013.01); *A61B 6/107* (2013.01); *A61B 6/4241* (2013.01); *G06T 11/006* (2013.01); *A61B 6/545* (2013.01)

(58) Field of Classification Search

CPC ........... A61B 6/032; A61B 6/54; A61B 6/542; A61B 6/486; A61B 6/545; A61B 2576/00; A61B 5/7217; A61B 5/7289; A61B 6/03; G06T 2207/10081

See application file for complete search history.

(56) References Cited

U.S. PATENT DOCUMENTS 9,554,760 B2 1/2017 Rodrigues et al.
2004/0017224 A1* 1/2004 Tumer ................ H04N 25/773 327/51

FOREIGN PATENT DOCUMENTS

CN 104812305 B 3/2018

* cited by examiner

*Primary Examiner* — Don K Wong

(57) ABSTRACT

A medical imaging method is disclosed. The medical imaging method includes: controlling, based on an emission cycle, a ray generator to emit a periodic imaging signal; emitting, based on a reset cycle, a reset signal for resetting, when the ray generator stops emitting the periodic imaging signal, a ray detector, controlling the reset ray detector to receive the periodic imaging signal; and performing, based on the received periodic imaging signal, image reconstruction to generate a medical image. And a medical imaging device and an electronic apparatus are also disclosed.

20 Claims, 8 Drawing Sheets

MEDICAL IMAGING METHOD, DEVICE, AND ELECTRONIC APPARATUS

CROSS-REFERENCE TO RELATED APPLICATIONS

The present application claims priority to Chinese patent application No. 202211738761.8, filed on Dec. 30, 2022, the entire contents of which are incorporated herein by reference.

TECHNICAL FIELD

The present disclosure relates to the field of imaging, and more particularly, to medical imaging methods and devices.

BACKGROUND

Photon counting detectors have led human X-ray detection technology into a new era. Photon counting imaging can directly obtain energy levels of photons and the corresponding number of photons, thereby realizing multi-energy domain imaging, and broadening the prospect and development of the X-ray detection technology in the medical field.

However, under long-term irradiation the photon counting detector applied to the medical field causes the physical characteristics of a crystal of the photon counting detector and the charge response characteristics of a readout circuit of the photon counting detector to change, and causes the detector to generate a non-uniform counting response to incident X-rays, thereby affecting the imaging quality of medical images.

SUMMARY

The present disclosure provides a medical imaging method and device, and an electronic apparatus, which can overcome the defect of the photon counting detector in the conventional art that the imaging quality of the medical image is affected by the photon counting detector under long-term irradiation.

A first aspect of the present disclosure provides a medical imaging method. The medical imaging method includes controlling, based on an emission cycle, a ray generator to emit a periodic imaging signal; emitting, based on a reset cycle, a reset signal for resetting, when the ray generator stops emitting the periodic imaging signal, a ray detector; controlling the reset ray detector to receive the periodic imaging signal; and performing, based on the received periodic imaging signal, image reconstruction to generate a medical image.

In the first aspect of the present disclosure, the medical imaging method further includes: determining a radiation intensity of the periodic imaging signal; and configuring, based on the radiation intensity, the reset cycle for the reset signal.

In the first aspect of the present disclosure, the reset cycle includes a reset time, and the configuring, based on the radiation intensity, the reset cycle for the reset signal includes: setting, when the radiation intensity is greater than or equal to a predetermined intensity threshold, the reset time of the reset cycle to be at a gap time following each emission of the periodic imaging signal.

In the first aspect of the present disclosure, the configuring, based on the radiation intensity, the reset cycle for the reset signal includes: setting, when the radiation intensity is less than the predetermined intensity threshold, the reset time of the reset cycle to be at a gap time following at least two consecutive emissions of the periodic imaging signal.

In the first aspect of the present disclosure, the ray generator includes a bulb tube. The controlling, based on the emission cycle, the ray generator to emit the periodic imaging signal includes: controlling, based on the emission cycle, the bulb tube to emit an imaging signal periodically, to generate the periodic imaging signal.

In the first aspect of the present disclosure, the ray generator includes a periodic shielding device, and a bulb tube configured to emit an image signal. The controlling, based on the emission cycle, the ray generator to emit the periodic imaging signal includes: controlling, based on the emission cycle, the periodic shielding device to shield the imaging signal emitted by the bulb tube periodically.

In the first aspect of the present disclosure, the medical imaging method further includes: determining, based on a predetermined first periodic pulse signal, the emission cycle; and determining, based on a predetermined second periodic pulse signal, the reset cycle, the second periodic pulse signal having an opposite phase to the first periodic pulse signal.

In the first aspect of the present disclosure, each of the first periodic pulse signal and the second periodic pulse signal is configured according to a user input, or automatically configured according to a user protocol.

In the first aspect of the present disclosure, the medical imaging method further includes: determining a radiation intensity of the periodic imaging signal; and adjusting, based on the radiation intensity, the emission cycle for the periodic imaging signal.

In the first aspect of the present disclosure, the adjusting, based on the radiation intensity, the emission cycle for the periodic imaging signal includes: adjusting, when the radiation intensity is greater than a preset intensity threshold, the periodic imaging signal to be emitted periodically at equal intervals; and adjusting, when the radiation intensity is less than or equal to the preset intensity threshold, the periodic imaging signal to be emitted periodically at varying intervals.

In the first aspect of the present disclosure, the performing, based on the received periodic imaging signal, the image reconstruction to generate the medical image includes: generating, based on the received periodic imaging signal, sparse sampling data; and reconstructing, by a reconstruction device, the sparse sampling data to generate the medical image.

In the first aspect of the present disclosure, the controlling the reset ray detector to receive the periodic imaging signal includes: determining, based on a predetermined first periodic pulse signal, a reception cycle for the periodic imaging signal; and controlling, based on the reception cycle, the reset ray detector to receive the periodic imaging signal.

A second aspect of the present disclosure provides a medical imaging device. The medical imaging device includes: a ray generator configured to emit, based on an emission cycle, a periodic imaging signal; a ray detector configured to receive the periodic imaging signal emitted by the ray generator; and a reset circuit connected to the ray detector, and configured to emit, based on a reset cycle, a reset signal for resetting, when the ray detector stops receiving the periodic imaging signal, the ray detector.

In the second aspect of the present disclosure, the medical imaging device further includes: a reconstruction device connected to the ray detector, and configured to perform, based on the received periodic imaging signal, image reconstruction to generate a medical image.

In the second aspect of the present disclosure, the ray generator is further configured to determine the emission cycle, and the reset circuit is further configured to determine the reset cycle.

In the second aspect of the present disclosure, the reset circuit is further configured to: set, when a radiation intensity of the periodic imaging signal is greater than or equal to a predetermined intensity threshold, a reset time of the reset cycle to be at a gap time following each emission of the periodic imaging signal; and set, when the radiation intensity is less than the predetermined intensity threshold, the reset time of the reset cycle to be at a gap time following at least two consecutive emissions of the periodic imaging signal.

In the second aspect of the present disclosure, the ray generator is further configured to: adjust, when a radiation intensity of the periodic imaging signal is greater than a preset intensity threshold, the periodic imaging signal to be emitted periodically at equal intervals; and adjust, when the radiation intensity is less than or equal to the preset intensity threshold, the periodic imaging signal to be emitted periodically at varying intervals.

In the second aspect of the present disclosure, the ray generator includes a bulb tube configured to emit, based on the emission cycle, the imaging signal periodically, to generate the periodic imaging signal.

In the second aspect of the present disclosure, the ray generator includes: a bulb tube configured to emit an image signal; and a periodic shielding device configured to shield, based on the emission cycle, the imaging signal emitted by the bulb tube periodically.

A third aspect of the present disclosure provides an electronic apparatus. The electronic apparatus includes a memory, a processor, and a computer program stored in the memory and executable on the processor. The computer program, when executed by the processor, causes the processor to perform the medical imaging method according to the first aspect.

A fourth aspect of the present disclosure provide a non-volatile computer-readable storage medium having a computer program stored therein. The computer program, when executed by a processor, causes the processor to perform the medical imaging method according to the first aspect.

DETAILED DESCRIPTION OF THE EMBODIMENTS

The present disclosure is further described below by way of exemplary embodiments, but the present disclosure is not therefore limited to the scope of the described embodiments.

Figure 1:
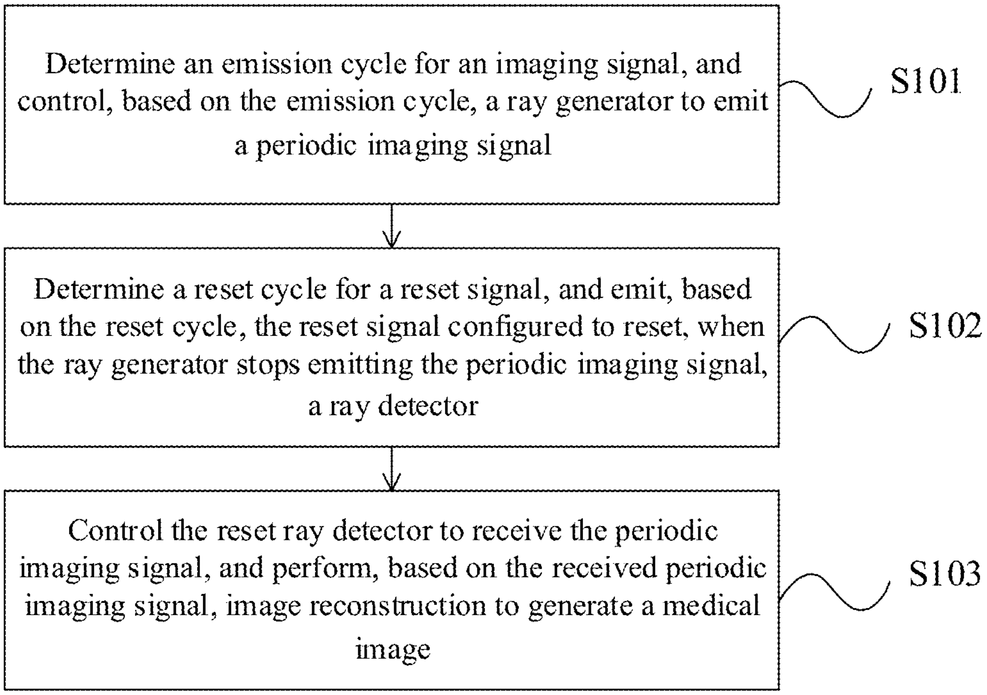
FIG. 1 is a flow diagram illustrating a medical imaging method according to an exemplary embodiment of the present disclosure.

FIG. 1 is a flow diagram illustrating a medical imaging method according to an exemplary embodiment of the present disclosure. The medical imaging method is applicable to any one or more imaging apparatuses such as a computed tomography (CT) equipment, an X-ray imaging equipment, or a fluoroscopy machine. The CT equipment may be any one of an energy-integrating CT equipment, a photon counting CT equipment, or a micro computed tomography (micro-CT) equipment. The medical imaging method according to this embodiment can be applied to the photon counting CT equipment. The photon counting CT equipment uses a photon detector as a ray detector to receive an imaging signal. Compared with traditional energy-integrating CT equipment, the photon counting CT equipment exhibits superior spatial resolution and soft tissue contrast, while reducing noise, blooming, and beam-hardening artifacts.

Referring to FIG. 1, in step S101, an emission cycle for an imaging signal is determined, and a ray generator is controlled to emit a periodic imaging signal based on the emission cycle.

The imaging signal may be an X-ray, but is not limited to the X-ray. The imaging signal may be selected from a variety of rays for imaging according to actual imaging requirements. The ray generator emits the periodic imaging signal based on the emission cycle. Each emission cycle includes an emission time when the periodic imaging signal is emitted and a gap time when the emission of the periodic imaging signal is stopped. The emission cycle repeats to complete a medical imaging for a subject to be imaged.

In this embodiment, the problem of inconsistent charge response caused by a long period of continuous operation of the ray detector is avoided by periodically emitting the imaging signal, and the impact of residual charge on the ray detector is eliminated during the gap time when the emission cycle is stopped, thereby restoring the ray detector to its initial state.

Figure 2:
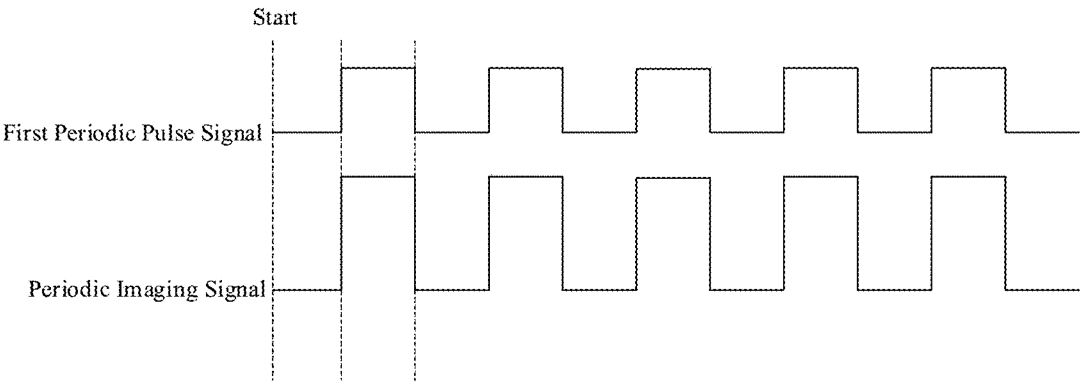
FIG. 2 is a schematic diagram illustrating an emission cycle for an imaging signal controlled by a first periodic pulse signal according to an exemplary embodiment of the present disclosure.

In some embodiments, the determining the emission cycle in step S101 specifically includes: determining the emission cycle for the imaging signal based on a predetermined first periodic pulse signal. FIG. 2 is a schematic diagram illustrating the emission cycle for the imaging signal controlled by the first periodic pulse signal. Referring to FIG. 2, when a pulse level of the first periodic pulse signal is high, the ray generator is controlled to emit the periodic imaging signal once. When the pulse level of the first periodic pulse signal is low, the ray generator is controlled to stop emitting the periodic imaging signal.

The first periodic pulse signal is generated by a pulse generating circuit, and the first periodic pulse signal acts on the ray generator. The pulse generating circuit may be built in an internal circuit of the ray generator, or may be arranged outside the ray generator.

In an implementation, the first periodic pulse signal may be configured according to a user input, and parameters for the pulse characteristics of the first periodic pulse signal are configured by the pulse generating circuit. The pulse characteristics include: a pulse shape, a pulse width, or a duty cycle of the pulse. A user may directly select one or more of the above pulse characteristics for parameter configuration.

In an implementation, the first periodic pulse signal may be automatically configured according to a user protocol. The user protocol is determined before performing the medical imaging of the subject to be imaged. The user protocol includes an integration time per field of view for each ray detector to acquire the periodic imaging signal, a current value, and a voltage value, etc., configured at the ray generator. The pulse generating circuit selects the parameters for the pulse characteristics that adaptively match the user protocol, and then the pulse generating circuit generates a corresponding periodic pulse signal according to the parameters for the pulse characteristics. Specifically, a single pulse duration of the first periodic pulse signal is obtained according to the integration time per field of view, and it is determined whether a value of the current parameter setting exceeds a threshold value for switching the pulse period scheme according to a bulb tube voltage value and a bulb tube current value.

It should be noted that, referring to FIG. 2, the emission time for the periodic imaging signal in a single emission cycle may be adjusted by configuring the pulse width of the first periodic pulse signal. The wider the pulse width, the longer the emission time of each emission cycle, and vice versa. The gap time for stopping the emission of the imaging signal in the single emission cycle may be adjusted by configuring the duty cycle of the first periodic pulse signal. The larger the duty cycle, the shorter the gap time of each emission cycle, and vice versa.

In some embodiments, the ray generator includes a bulb tube. The controlling, based on the emission cycle, the ray generator to emit the periodic imaging signal in step S101 specifically includes: controlling the bulb tube to periodically emit an imaging signal based on the emission cycle to generate the periodic imaging signal.

In an implementation, the bulb tube is controlled by the first periodic pulse signal to periodically emit the imaging signal to generate the periodic imaging signal. When the pulse level of the first periodic pulse signal is high, the bulb tube is controlled to emit the periodic imaging signal once. When the pulse level of the first periodic pulse signal is low, the bulb tube is controlled to stop emitting the periodic imaging signal.

In some embodiments, the ray generator includes a periodic shielding device and a bulb tube. The controlling, based on the emission cycle, the ray generator to emit the periodic imaging signal in step S101 specifically includes: controlling the periodic shielding device to periodically shield the imaging signal emitted by the bulb tube based on the emission cycle.

In an implementation, the bulb tube is controlled to emit the imaging signal, and the periodic shielding device is controlled by the first periodic pulse signal to periodically shield the imaging signal emitted by the bulb tube to generate the periodic imaging signal. When the pulse level of the first periodic pulse signal is high, the periodic shielding device is controlled not to shield the periodic imaging signal emitted by the bulb tube. When the pulse level of the first periodic pulse signal is low, the periodic shielding device is controlled to shield the periodic imaging signal emitted by the bulb tube.

Referring to FIG. 1, in step S102, a reset cycle for a reset signal is determined, and the reset signal is emitted based on the reset cycle. The reset signal is used to reset a ray detector when the ray generator stops emitting the periodic imaging signal.

The reset signal is generated by a reset circuit, and the reset signal acts on the ray detector to reduce the residual charge on the ray detector. Generally, the ray detector may gradually return to the initial state after stopping receiving the imaging signal, and a recovery time is as long as tens of minutes. Therefore, the recovery of the ray detector to the initial state may be further accelerated by the reset signal. The reset circuit emits the reset signal based on the reset cycle. Each reset cycle includes a reset time when the reset signal is emitted and a stop time when the emission of the reset signal is stopped. The reset cycle repeats to complete the medical imaging of the subject to be imaged.

During the action of the reset signal, the ray detector does not receive the periodic imaging signal and does not generate imaging data, thus avoiding a negative impact of the reset signal on the imaging data of the ray detector, which makes an imaging result of a medical image inaccurate, and thus affects a subsequent use of the medical image. The ray detector is reset after receiving the reset signal, so that the responsiveness of the ray detector to the imaging signal is restored to the initial state.

In some embodiments, the reset signal may include a reset pulse signal or an interference energy signal. The interference energy signal includes but is not limited to: any one or more of thermal energy, electromagnetic wave, ultraviolet light, visible light, or infrared light. When the reset signal is the reset pulse signal, the reset circuit may be built in an internal circuit of the ray detector. When the reset signal is the interference energy signal, the reset circuit may be arranged outside the ray detector.

In some embodiments, the reset circuit applies the reset signal to the ray detector during an intermittent time when the ray generator stops emitting the periodic imaging signal, or applies the reset signal to the ray detector during an intermittent time when the ray detector stops receiving the periodic imaging signal, thereby accelerating the recovery process of the ray detector.

Figure 3:
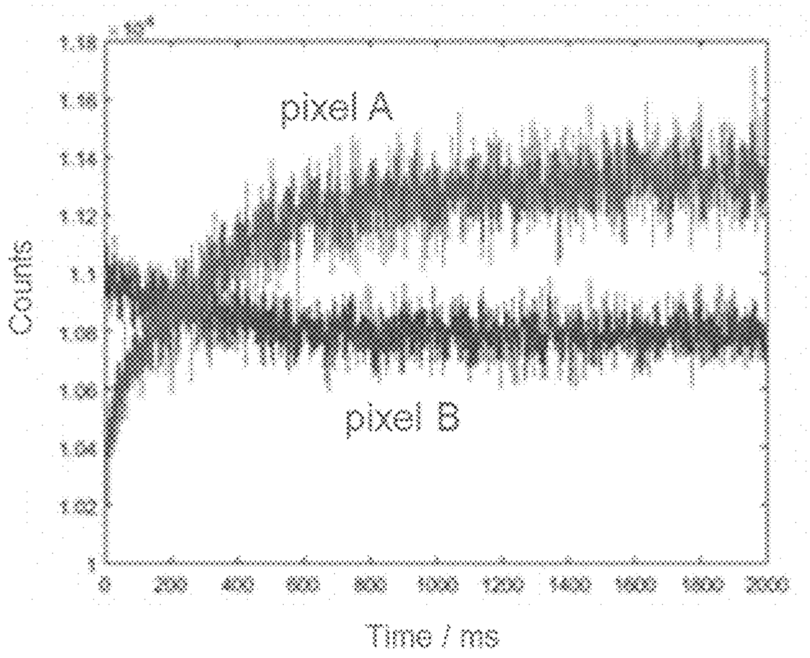
FIG. 3 is a schematic diagram illustrating a change in counts with time of a photon counting detector of a photon counting CT equipment under long-term continuous X-ray irradiation according to an exemplary embodiment of the present disclosure.

Taking the photon counting CT equipment as an example, FIG. 3 is a schematic diagram illustrating a change in counts with time of a photon counting detector of a photon counting CT equipment under long-term continuous X-ray irradiation. The counts in FIG. 3 are acquired by the photon counting detector in real time. It can be seen that under the long-term X-ray irradiation, a pixel A and a pixel B of the photon counting detector inevitably produce a non-uniform response to the incident X-ray in time and space. This deteriorated response can be described as that under the long-term X-ray irradiation, the response characteristics of the detector require a period of time to return to a new stable state. It can be seen from FIG. 3 that the formation time of this deteriorated response is on the order of hundreds of milliseconds. In this embodiment, the reset signal allows the pixels of the photon detector to obtain a certain period of intermittent time to return to the initial operating state after each stopping the emission of the periodic imaging signal (i.e., X-ray). For example, the reset cycle for each emitting the reset signal is on the order of hundreds of microseconds. Therefore, the detector may be controlled to return to the initial operating state before the deteriorated response occurs in the detector, thereby reducing the occurrence of the deteriorated response, and improving the imaging quality of the medical image.

Figure 4:
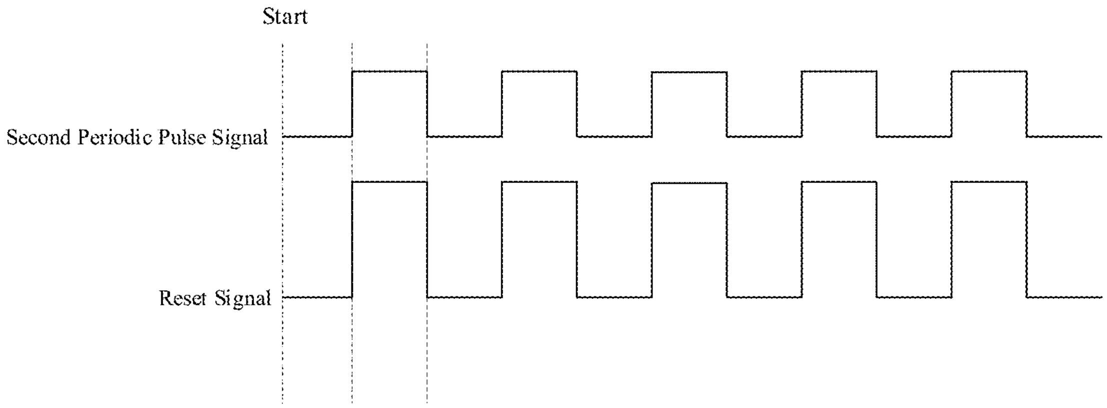
FIG. 4 is a schematic diagram illustrating a reset cycle for a reset signal controlled by a second periodic pulse signal according to an exemplary embodiment of the present disclosure.

In some embodiments, the determining the reset cycle in step S102 specifically includes: determining the reset cycle for the reset signal based on a predetermined second periodic pulse signal. The second periodic pulse signal has an opposite phase to the first periodic pulse signal. The second periodic pulse signal is generated by the pulse generating circuit, and the second periodic pulse signal acts on the reset signal. FIG. 4 is a schematic diagram illustrating the reset cycle for the reset signal controlled by the second periodic pulse signal. Referring to FIG. 4, when the pulse level of the second periodic pulse signal is high, the reset circuit is controlled to emit the reset signal once, and when the pulse level of the second periodic pulse signal is low, the reset circuit is controlled to stop emitting the reset signal.

In an implementation, the second periodic pulse signal may be set to have an opposite phase to the first periodic pulse signal, but have the same parameters for other pulse characteristics as the first periodic pulse signal.

In an implementation, the second periodic pulse signal may be configured according to a user input, and the parameters for the pulse characteristics of the second periodic pulse signal are configured by the pulse generating circuit. The pulse characteristics include: a pulse shape, a pulse width, or a duty cycle of the pulse.

In an implementation, the second periodic pulse signal may be automatically configured according to a user protocol. The user protocol is determined before the medical imaging of the subject to be imaged. The user protocol includes an integration time per field of view for each ray detector to acquire the periodic imaging signal, a current value, and a voltage value, etc., configured at the ray generator. The pulse generating circuit selects the parameters of the pulse characteristics that adaptively match the user protocol, and then the pulse generating circuit generates a corresponding periodic pulse signal according to the parameters of the pulse characteristics. Specifically, a single pulse duration of the first periodic pulse signal is obtained according to the integration time per field of view, and it is determined whether a value of the current parameter setting exceeds a threshold value for switching the pulse period scheme according to a bulb tube voltage value and a bulb tube current value.

In some embodiments, the determining the reset cycle for the reset signal in step S102 specifically includes: determining a radiation intensity of the periodic imaging signal, and configuring the reset cycle for the reset signal based on the radiation intensity.

In an implementation, the ray intensity of the periodic imaging signal may be determined based on the periodic imaging signal acquired in real time. Specifically, real-time acquisition can be performed in the following ways. Firstly, the periodic imaging signal received by the ray generator is acquired in real time. Secondly, the ray intensity is determined based on a current intensity of the periodic imaging signal emitted by the ray generator, and the stronger the current intensity is, the stronger the ray intensity of the imaging signal is, and vice versa. Different ray intensities act on the ray detector, causing the ray detector to generate a deteriorated response for different lengths of time. The stronger the ray intensity, the easier it is for the ray detector to reach an undesirable state where the deteriorated response is generated. Therefore, when the ray intensity becomes stronger, the reset time and emission frequency of the reset signal need to be increased.

In an implementation, the ray intensity of the periodic imaging signal may be determined according to a user protocol. The user protocol is determined before the medical imaging of the subject to be imaged. The user protocol includes a current value, and a voltage value, etc., configured at the ray generator. The ray intensity of the periodic imaging signal may be determined according to the current configured at the ray generator.

In an implementation, the configuring, based on the radiation intensity, the reset cycle for the reset signal specifically includes the following steps.

When the radiation intensity is greater than or equal to a predetermined intensity threshold, the reset time of the reset cycle is configured to be at a gap time following each emission of the periodic imaging signal. The intensity threshold may be configured according to an actual application scenario. It can further be understood that, referring to FIG. 5, when the ray generator emits the periodic imaging signal, the reset circuit stops emitting the reset signal, and when the ray generator stops emitting the periodic imaging signal, the reset circuit emits the reset signal. The two alternately reciprocate at the same frequency until the imaging of the medical image is completed.

When the radiation intensity is less than the predetermined intensity threshold, the reset time of the reset cycle is configured to be at a gap time following at least two consecutive emissions of the periodic imaging signal. It can be further understood that, referring to FIG. 6, when the ray generator emits the periodic imaging signal, the reset circuit stops emitting the reset signal, and when the ray generator stops emitting the periodic imaging signal after emitting the periodic imaging signal at least twice, the reset circuit emits the reset signal. The two reciprocate until the imaging of the medical image is completed.

In some embodiments, the emission cycle of the periodic imaging signal may also be adjusted according to the ray intensity.

Figure 5:
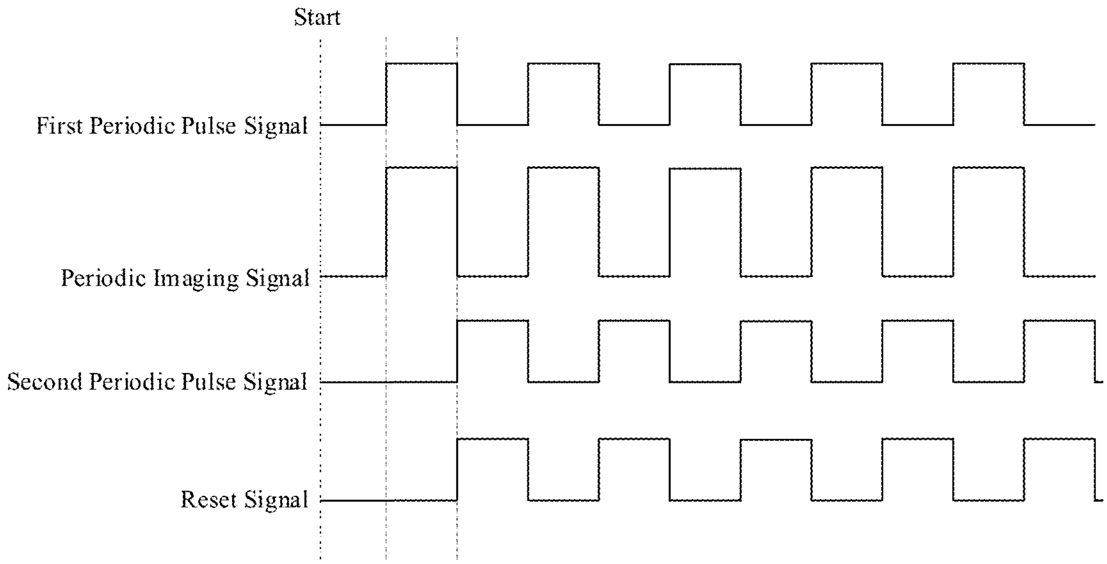
FIG. 5 is a schematic diagram illustrating a periodic imaging signal and a reset signal when a radiation intensity is greater than or equal to a predetermined intensity threshold according to an exemplary embodiment of the present disclosure.

When the ray intensity is greater than a predetermined intensity threshold, the periodic imaging signal is configured to be emitted periodically at equal intervals. That is, the emission time for each emitting the periodic imaging signal in FIG. 5 is the same as the gap time for stopping the emission of the periodic imaging signal, so as to give the ray detector a certain recovery time to recover following each emission of the periodic imaging signal, thereby preventing the ray detector from reaching the undesirable state where the deteriorated response is generated when the periodic imaging signal is emitted under a strong ray intensity condition.

Figure 6:
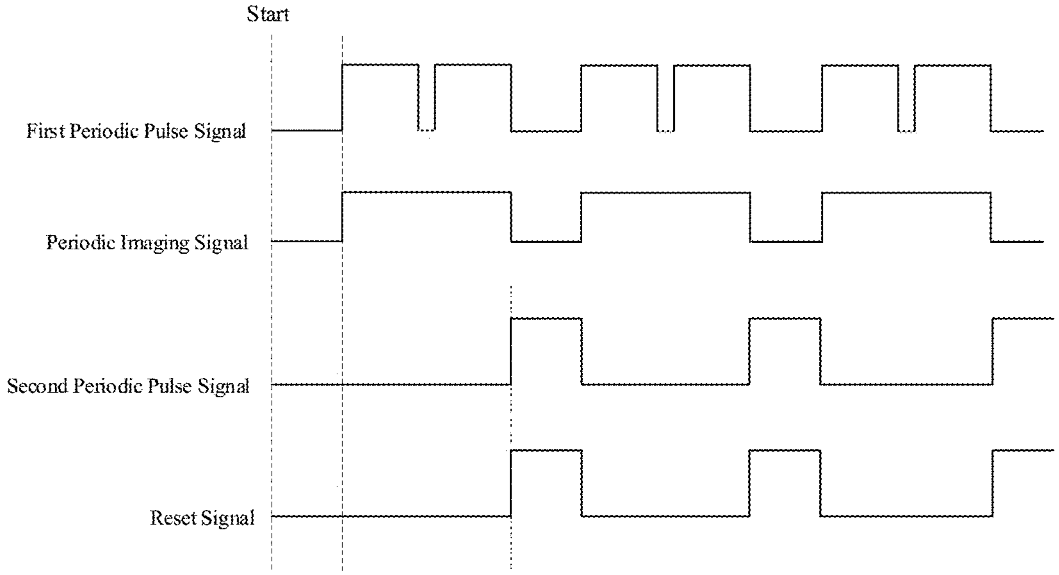
FIG. 6 is a schematic diagram illustrating a periodic imaging signal and a reset signal when a radiation intensity is less than an intensity threshold according to an exemplary embodiment of the present disclosure.

When the ray intensity is less than or equal to the predetermined intensity threshold, the periodic imaging signal is configured to be periodically emitted at varying intervals. That is, the emission time for each emitting the periodic imaging signal in FIG. 6 is greater than the gap time for stopping the emission of the periodic imaging signal. While preventing the ray detector from reaching the undesirable state where the deteriorated response is generated, extending the emission time of each emission of the periodic imaging signal is conducive to increasing a sampling density of imaging, thereby improving the imaging quality of the medical image.

In this embodiment, by matching the reset cycle for the reset signal with the emission cycle for the periodic imaging signal, the ray detector can be restored from the state where the deteriorated response is generated in time without affecting the imaging result, and the imaging quality of the medical image can be improved.

Referring to FIG. 1, in step S103, the reset ray detector is controlled to receive the periodic imaging signal, and image reconstruction is performed to generate a medical image based on the received periodic imaging signal.

In some embodiments, the ray detector generates sparse sampling data based on the received periodic imaging signal, and the sparse sampling data is reconstructed by a reconstruction device to generate the medical image. The reconstruction device may be integrated with the ray detector, or separated to the ray detector. And the reconstruction device may be implemented as hardware, for example, at least part of an application specific integrated circuit, or software, for example, program instructions executable by at least one processor.

Figure 7:
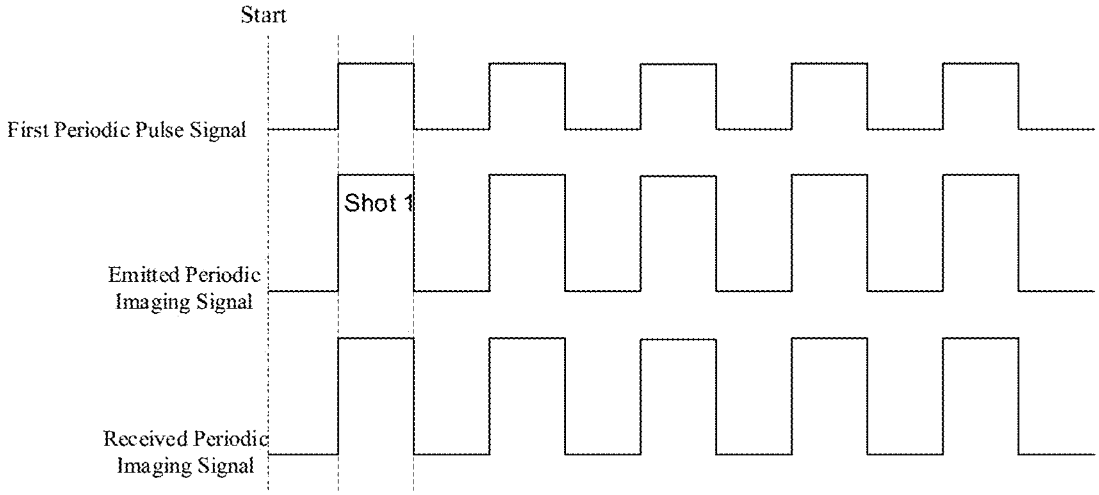
FIG. 7 is a schematic diagram illustrating a reception cycle of an imaging signal controlled by a first periodic pulse signal according to an exemplary embodiment of the present disclosure

In some embodiments, the ray detector may receive the periodic imaging signal based on a reception cycle. Referring to FIG. 7, the reception cycle may be configured the same as the emission cycle to synchronize the states of the ray generator and the ray detector. In addition, the reception cycle may be used for subsequent reconstruction of the sparse sampling data.

In some embodiments, the reception cycle for the periodic imaging signal is determined based on a predetermined first periodic pulse signal. The first periodic pulse signal is generated by the pulse generating circuit, and the first periodic pulse signal acts on the ray generator. FIG. 7 is a schematic diagram illustrating the reception cycle for the imaging signal controlled by the first periodic pulse signal. Referring to FIG. 7, when the pulse level of the first periodic pulse signal is high, the ray detector is controlled to receive the periodic imaging signal once, and when the pulse level of the first periodic pulse signal is low, the ray detector is controlled to stop receiving the periodic imaging signal.

In some embodiments, a sparse sampling reconstruction algorithm is a technology that uses an energy attenuation of the imaging signal to calculate and image. The traditional reconstruction algorithm needs to use complete projection data of the imaging signal to obtain an ideal reconstruction result, while the sparse sampling reconstruction algorithm does not need to obtain complete projection data of the imaging signal. The algorithms used for the reconstruction of the sparse sampling data in the reconstruction device include, but are not limited to, a K-space weighted image contrast (KWIC) reconstruction scheme, a projection window sharing reconstruction technology, a compressed sensing sparse reconstruction technology, or a deep learning neural network reconstruction technology.

According to the above medical imaging method, the impact of the charge accumulation of the ray detector on the imaging quality of the medical image can be eliminated by periodically emitting the imaging signal based on an emission cycle. In addition, the reset signal is emitted to reset the state of the ray detector during the imaging interval of the periodic imaging signal, so as to accelerate the recovery of the ray detector, thereby improving the efficiency and quality of the medical imaging and ensuring the stability of the medical imaging device.

Figure 8:
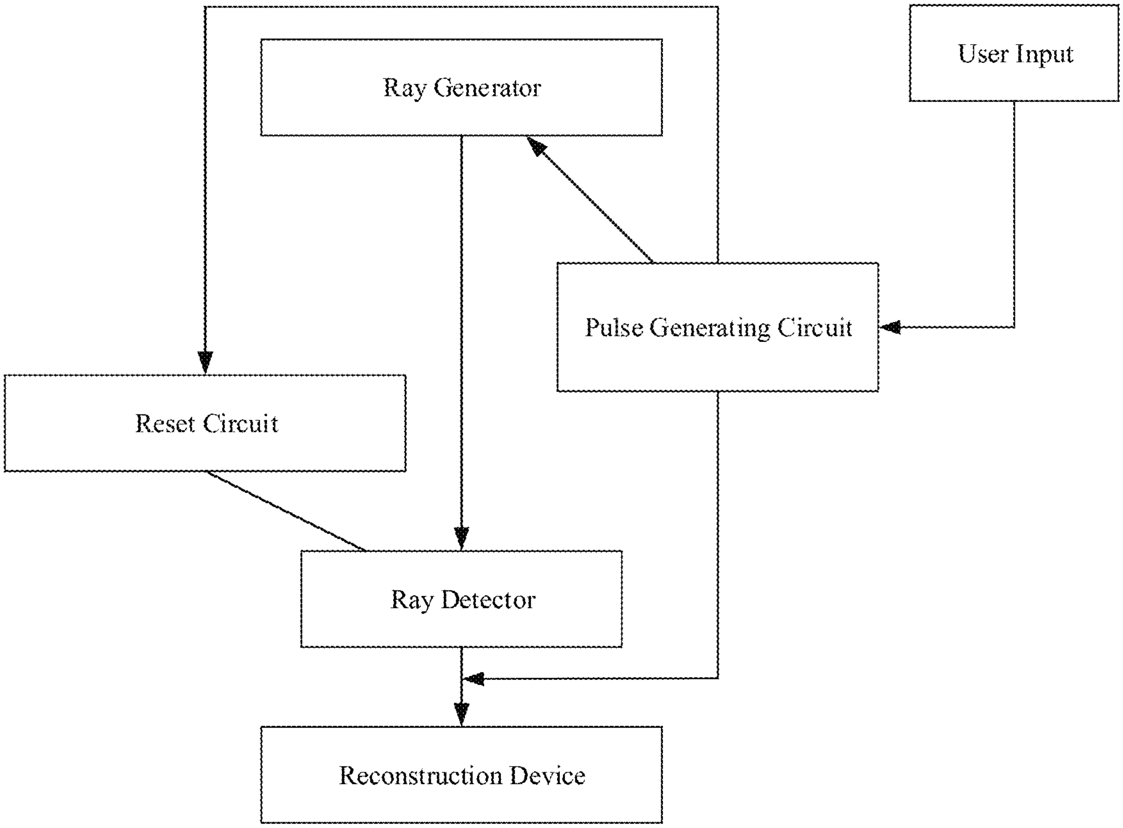
FIG. 8 is a schematic diagram illustrating a system to which a medical imaging device according to an exemplary embodiment of the present disclosure is applied.

An exemplary system to which the above-described medical imaging method is applied is described in detail below with reference to FIG. 8. The system includes a user input, a pulse generating circuit, a ray generator, a ray detector, a reset circuit and a reconstruction device.

The user inputs imaging requirements of the subject to be imaged into the pulse generating circuit. The pulse generating circuit selects parameters for the pulse characteristics that adaptively match the imaging requirements, and the pulse generating circuit generates corresponding first periodic pulse signal and second periodic pulse signal based on the parameters for the pulse characteristics.

The first periodic pulse signal acts on the ray generator and the ray detector, respectively. Under the action of the first periodic pulse signal, the ray generator emits the periodic imaging signal based on the emission cycle, and the ray detector receives the periodic imaging signal based on the reception cycle. The emission cycle and the reception cycle match each other to avoid missing the imaging signal and affecting the accuracy and completeness of imaging of the medical image.

The second periodic pulse signal acts on the reset circuit. Under the action of the second periodic pulse signal, the reset circuit emits the reset signal to a detection crystal of the ray detector based on the reset cycle, so as to eliminate the residual charge on the detection crystal and accelerate the recovery of the ray detector to the initial state.

The reset signal and the periodic imaging signal are alternately emitted to the ray detector, and the reset circuit emits the reset signal only during the gap time when the ray generator stops emitting the periodic imaging signal. The specific reset cycle for the reset signal may be configured based on the periodic imaging signal. The stronger the intensity of the periodic imaging signal, the longer the reset time of the reset signal, and the higher the reset frequency of the reset signal. The weaker the intensity of the periodic imaging signal, the shorter the reset time of the reset signal, and the lower the reset frequency of the reset signal.

Figure 9:
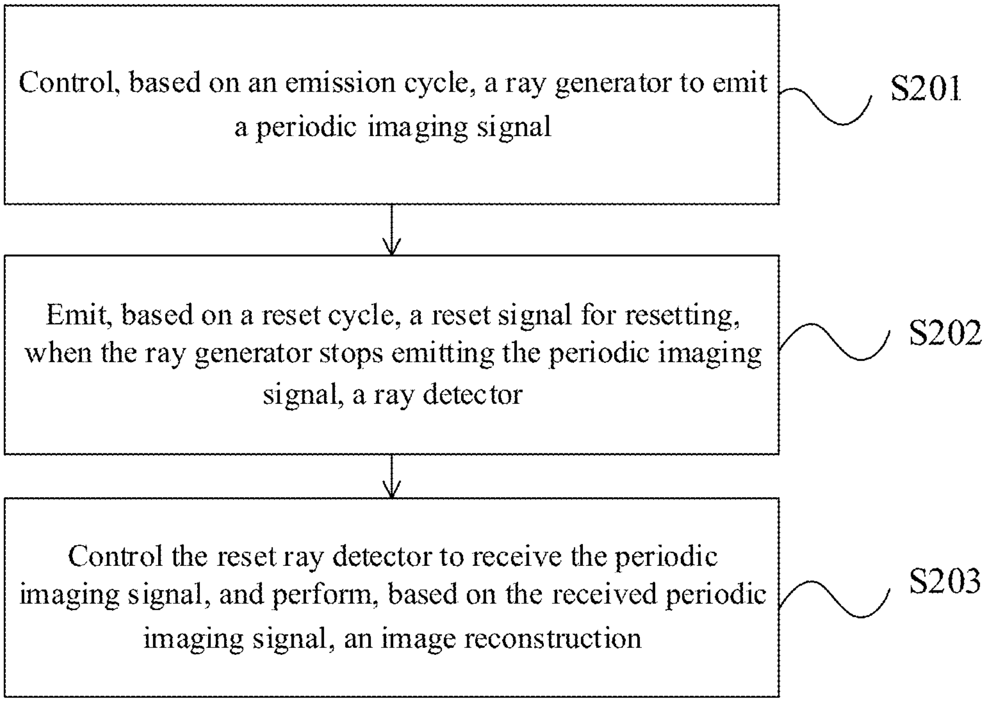
FIG. 9 is a flow diagram illustrating a medical imaging method according to another exemplary embodiment of the present disclosure.

FIG. 9 is a flow diagram illustrating a medical imaging method according to another exemplary embodiment of the present disclosure. The medical imaging method according to this exemplary embodiment is substantially the same as the medical imaging method according to the exemplary embodiment shown in FIG. 1, except that the steps of determining the emission cycle and determining the reset cycle are omitted. Referring to FIG. 9, in this embodiment, the medical imaging method includes the following steps.

In step S201, a ray generator is controlled to emit a periodic imaging signal based on an emission cycle.

In this step, the ray generator emits the periodic imaging signal based on the emission cycle. The emission cycle is determined based on a first periodic pulse signal generated by a pulse generating circuit. As described above, the first periodic pulse signal may be configured according to a user input, or may be automatically configured according to a user protocol.

In step S202, the reset signal is emitted based on a reset cycle. The reset signal is used to reset a ray detector when the ray generator stops emitting the periodic imaging signal.

In this step, the reset signal is emitted by, for example, a reset circuit in accordance with a reset cycle. The reset cycle is determined based on a second periodic pulse signal generated by the pulse generating circuit. As described above, the second periodic pulse signal may be configured according to a user input, or may be automatically configured according to a user protocol.

In step S203, the reset ray detector is controlled to receive the periodic imaging signal, and image reconstruction is performed based on the received periodic imaging signal.

For details of the steps of the medical imaging method in this embodiment, reference may be made to the description made above with respect to the medical imaging method shown in FIG. 1, and details are not described herein again.

Figure 10:
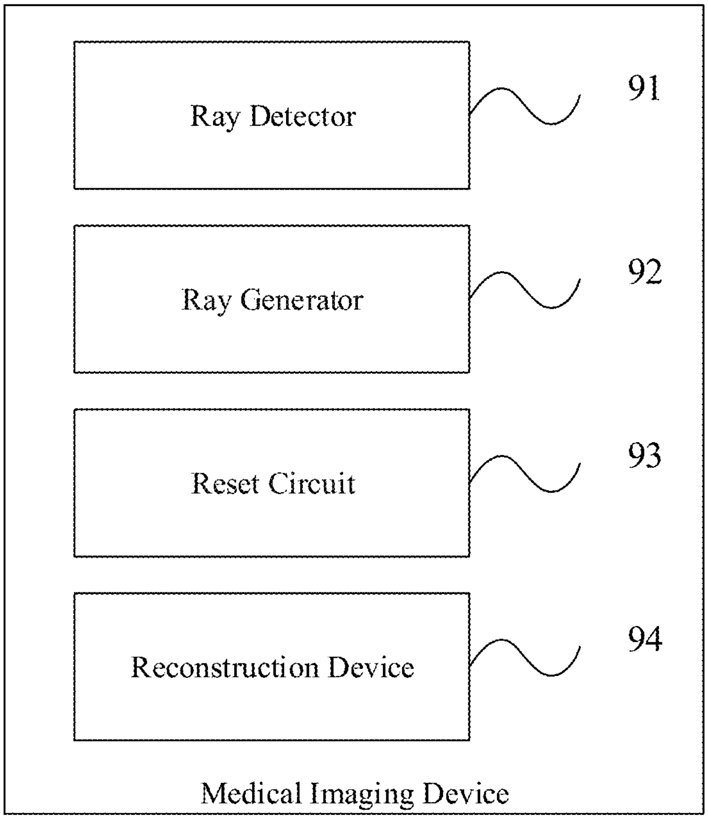
FIG. 10 is a diagram illustrating a configuration of a medical imaging device according to an exemplary embodiment of the present disclosure.

FIG. 10 is a diagram illustrating a configuration of a medical imaging device according to an exemplary embodiment of the present disclosure. Referring to FIG. 10, the medical imaging device includes a ray detector 91, a ray generator 92, a reset circuit 93, and a reconstruction device 94. The ray generator 92 is configured to determine an emission cycle for an imaging signal, and emit, based on the emission cycle, a periodic imaging signal. The reset circuit 93 is connected to the ray detector 91, and configured to determine a reset cycle for a reset signal, and emit, based on the reset cycle, the reset signal. The reset signal is used to reset the ray detector when the ray detector stops receiving the periodic imaging signal. The ray detector 91 is configured to receive the periodic imaging signal emitted by the ray generator after reset. The reconstruction device 94 is connected to the ray detector, and configured to perform, based on the received periodic imaging signal, image reconstruction to generate a medical image.

Figure 11:
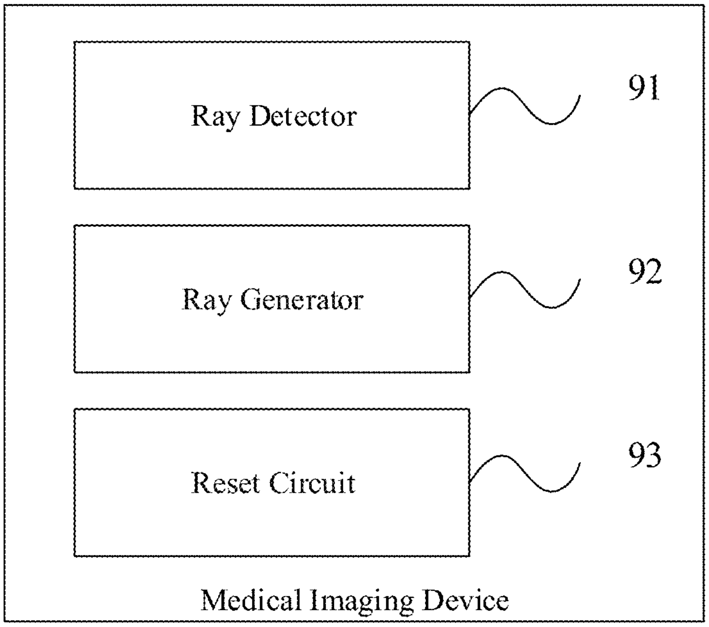
FIG. 11 is a diagram illustrating a configuration of a medical imaging device according to another exemplary embodiment of the present disclosure.

FIG. 11 is a diagram illustrating a configuration of a medical imaging device according to another exemplary embodiment of the present disclosure. The medical imaging device according to this exemplary embodiment is substantially the same as the medical imaging apparatus according to the exemplary embodiment shown in FIG. 10, except that the reconstruction device is omitted. Referring to FIG. 11, the medical imaging device includes: a ray detector 91, a ray generator 92, and a reset circuit 93. The ray generator 92 is configured to emit a periodic imaging signal based on an emission cycle. The reset circuit 93 is connected to the ray detector 91, and configured to emit, based on a reset cycle, a reset signal. The reset signal is used to reset the ray detector when the ray detector stops receiving the periodic imaging signal. The ray detector 91 is configured to receive the periodic imaging signal emitted by the ray generator.

In some embodiments, the reset circuit 93 is further configured to: set, when a radiation intensity of the periodic imaging signal is greater than or equal to a predetermined intensity threshold, a reset time of the reset cycle to be at a gap time following each emission of the periodic imaging signal; and set, when the radiation intensity is less than the predetermined intensity threshold, the reset time of the reset cycle to be at a gap time following at least two consecutive emissions of the periodic imaging signal. The ray generator 92 is further configured to: adjust, when a radiation intensity of the periodic imaging signal is greater than a preset intensity threshold, the periodic imaging signal to be emitted periodically at equal intervals; and adjust, when the radiation intensity is less than or equal to the preset intensity threshold, the periodic imaging signal to be emitted periodically at varying intervals.

As for the device embodiment, since it substantially corresponds to the method embodiment, reference may be made to a partial description of the method embodiment. The above-described device embodiments are merely illustrative. The units described as separate components may or may not be physically separate, and the components shown as units may or may not be physical units. That is, they may be located in one place, or may be distributed on a plurality of network units. Some or all of these modules may be selected according to actual needs to achieve the purpose of the solution of the present disclosure. A person of ordinary skill in the art may understand and implement the embodiments without any creative effort.

Figure 12:
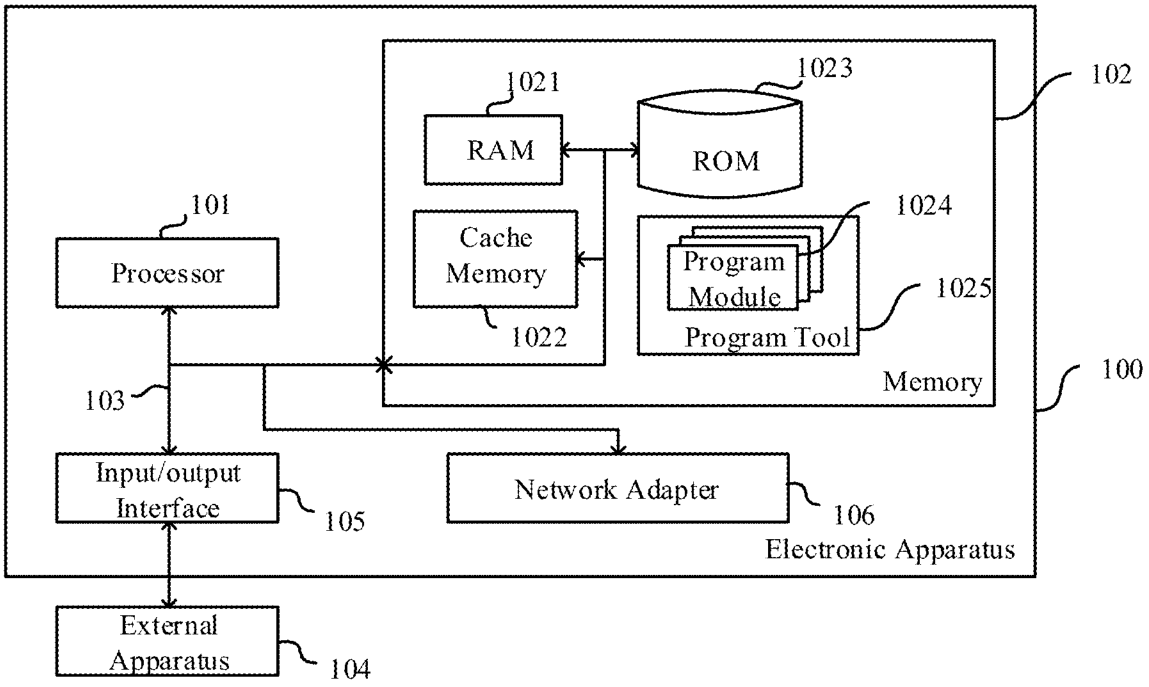
FIG. 12 is a diagram illustrating a configuration of an electronic apparatus according to an exemplary embodiment of the present disclosure.

FIG. 12 is a diagram illustrating a configuration of an electronic apparatus according to an exemplary embodiment of the present disclosure. The electronic apparatus 100 is suitable for implementing the above medical imaging method. The electronic apparatus 100 shown in FIG. 12 is only an example and should not constitute any limitation on the functions and scope of use of the embodiments of the present disclosure.

As shown in FIG. 12, the electronic apparatus 100 may be in the form of a general computing apparatus. For example, the electronic apparatus 100 may be a server. The components of the electronic apparatus 100 may include, but are not limited to: at least one processor 101, at least one memory 102, and a bus 103 connecting different system components (including the memory 102 and the processor 101).

The bus 103 includes a data bus, an address bus, and a control bus.

The memory 102 may include a volatile memory, such as a random-access memory (RAM) 1021 and/or a cache memory 1022, and may further include a read-only memory (ROM) 1023.

The memory 102 may also include a program tool 1025 (or a utility) having at least one set of program modules 1024. The program modules 1024 include, but are not limited to: an operating system, one or more applications, other program modules, and program data. Each or some combination of these examples may include an implementation of a network environment.

The processor 101 executes various functional applications and data processing by running computer programs stored in the memory 102, such as the method according to any of the above embodiments.

The electronic apparatus 100 may also communicate with one or more external apparatuses 104 through an input/output (I/O) interface 105. Moreover, the modularized electronic apparatus 100 may also communicate with one or more networks (e.g., a local area network (LAN), a wide area network (WAN), and/or a public network, such as the Internet) through a network adapter 107. As shown, the network adapter 107 communicates with other modules of the model-generated electronic apparatus 100 via the bus 103. It should be understood that, although not shown in the figures, other hardware and/or software modules may be used in conjunction with the model-generated electronic apparatus 100, including but not limited to: a microcode, a device driver, a redundant processor, an external disk drive array, a redundant array of independent disks (RAID), a tape drive, and a data backup storage system, etc.

It should be noted that although several units/modules or sub-units/modules of the electronic apparatus are mentioned in the above detailed description, this division is only exemplary and not mandatory. Indeed, according to embodiments of the present disclosure, the features and functions of two or more units/modules described above may be embodied in one unit/module. Conversely, the features and functions of one unit/module described above may be further divided to be embodied by a plurality of units/modules.

The embodiments of the present disclosure also provide a computer-readable storage medium, having a computer program stored therein. The computer program, when executed by a processor, implements the method according to any of the above embodiments.

More specifically, the readable storage medium may include, but is not limited to: a portable disk, a hard disk, a random-access memory, a read-only memory, an erasable programmable read-only memory, an optical storage device, a magnetic storage device, or any suitable combination of the above.

In an implementation, the embodiments of the present disclosure may also be implemented in the form of a program product including a program code. When the program product is run on a terminal device, the program code is configured to cause the terminal device to execute the method according to any of the above embodiments.

The program code for executing the present disclosure may be written in any combination of one or more programming languages. The program code may be executed entirely on the user's device, partly on the user's device, as a stand-alone software package, partly on the user's device and partly on a remote device, or entirely on the remote device.

Although specific embodiments of the present disclosure have been described above, a person skilled in the art will understand that these are only examples and the protection scope of the present disclosure is defined by the appended claims. The person skilled in the art may make various changes or modifications to these embodiments without departing from the principles and essence of the present disclosure, but these changes and modifications all fall within the protection scope of the present disclosure.

What is claimed is:

1. A medical imaging method comprising:

controlling, based on an emission cycle, a ray generator to emit a periodic imaging signal;

emitting, based on a reset cycle, a reset signal for resetting, when the ray generator stops emitting the periodic imaging signal, a ray detector;

controlling the reset ray detector to receive the periodic imaging signal; and performing, based on the received periodic imaging signal, image reconstruction to generate a medical image.

2. The medical imaging method of claim 1, further comprising:

determining a radiation intensity of the periodic imaging signal; and configuring, based on the radiation intensity, the reset cycle for the reset signal.

3. The medical imaging method of claim 2, wherein the reset cycle comprises a reset time, and wherein the configuring, based on the radiation intensity, the reset cycle for the reset signal comprises:

setting, when the radiation intensity is greater than or equal to a predetermined intensity threshold, the reset time of the reset cycle to be at a gap time following each emission of the periodic imaging signal.

4. The medical imaging method of claim 3, wherein the configuring, based on the radiation intensity, the reset cycle for the reset signal comprises:

setting, when the radiation intensity is less than the predetermined intensity threshold, the reset time of the reset cycle to be at a gap time following at least two consecutive emissions of the periodic imaging signal.

5. The medical imaging method of claim 1, wherein the ray generator comprises a bulb tube, and wherein the controlling, based on the emission cycle, the ray generator to emit the periodic imaging signal comprises:

controlling, based on the emission cycle, the bulb tube to emit an imaging signal periodically, to generate the periodic imaging signal.

6. The medical imaging method of claim 1, wherein the ray generator comprises a periodic shielding device, and a bulb tube configured to emit an image signal, and wherein the controlling, based on the emission cycle, the ray generator to emit the periodic imaging signal comprises:

controlling, based on the emission cycle, the periodic shielding device to shield the imaging signal emitted by the bulb tube periodically.

7. The medical imaging method of claim 1, further comprising:

determining, based on a predetermined first periodic pulse signal, the emission cycle; and determining, based on a predetermined second periodic pulse signal, the reset cycle, the second periodic pulse signal having an opposite phase to the first periodic pulse signal.

8. The medical imaging method of claim 7, each of the first periodic pulse signal and the second periodic pulse signal is configured according to a user input, or automatically configured according to a user protocol.

9. The medical imaging method of claim 1, further comprising:

determining a radiation intensity of the periodic imaging signal; and adjusting, based on the radiation intensity, the emission cycle for the periodic imaging signal.

10. The medical imaging method of claim 9, wherein the adjusting, based on the radiation intensity, the emission cycle for the periodic imaging signal comprises:

adjusting, when the radiation intensity is greater than a preset intensity threshold, the periodic imaging signal to be emitted periodically at equal intervals; and adjusting, when the radiation intensity is less than or equal to the preset intensity threshold, the periodic imaging signal to be emitted periodically at varying intervals.

11. The medical imaging method of claim 1, wherein the performing, based on the received periodic imaging signal, the image reconstruction to generate the medical image comprises:

generating, based on the received periodic imaging signal, sparse sampling data; and reconstructing, by a reconstruction device, the sparse sampling data to generate the medical image.

12. The medical imaging method of claim 1, wherein the controlling the reset ray detector to receive the periodic imaging signal comprises:

determining, based on a predetermined first periodic pulse signal, a reception cycle for the periodic imaging signal; and controlling, based on the reception cycle, the reset ray detector to receive the periodic imaging signal.

13. A medical imaging device comprising:

a ray generator configured to emit, based on an emission cycle, a periodic imaging signal;

a ray detector configured to receive the periodic imaging signal emitted by the ray generator; and a reset circuit connected to the ray detector, and configured to emit, based on a reset cycle, a reset signal for resetting, when the ray detector stops receiving the periodic imaging signal, the ray detector.

14. The medical imaging device of claim 13, further comprising:

a reconstruction device connected to the ray detector, and configured to perform, based on the received periodic imaging signal, image reconstruction to generate a medical image.

15. The medical imaging device of claim 13, wherein the ray generator is further configured to determine the emission cycle, and the reset circuit is further configured to determine the reset cycle.

16. The medical imaging device of claim 15, wherein the reset circuit is further configured to:

set, when a radiation intensity of the periodic imaging signal is greater than or equal to a predetermined intensity threshold, a reset time of the reset cycle to be at a gap time following each emission of the periodic imaging signal; and set, when the radiation intensity is less than the predetermined intensity threshold, the reset time of the reset cycle to be at a gap time following at least two consecutive emissions of the periodic imaging signal.

17. The medical imaging device of claim 15, wherein the ray generator is further configured to:

adjust, when a radiation intensity of the periodic imaging signal is greater than a preset intensity threshold, the periodic imaging signal to be emitted periodically at equal intervals; and adjust, when the radiation intensity is less than or equal to the preset intensity threshold, the periodic imaging signal to be emitted periodically at varying intervals.

18. The medical imaging device of claim 13, wherein the ray generator comprises a bulb tube configured to emit, based on the emission cycle, the imaging signal periodically, to generate the periodic imaging signal.

19. The medical imaging device of claim 13, wherein the ray generator comprises:

a bulb tube configured to emit an image signal; and a periodic shielding device configured to shield, based on the emission cycle, the imaging signal emitted by the bulb tube periodically.

20. An electronic apparatus comprising a memory, a processor, and a computer program stored in the memory and executable on the processor, wherein the computer program, when executed by the processor, causes the processor to:

control, based on an emission cycle, a ray generator to emit a periodic imaging signal;

emit, based on a reset cycle, a reset signal for resetting, when the ray generator stops emitting the periodic imaging signal, a ray detector;

control the reset ray detector to receive the periodic imaging signal; and perform, based on the received periodic imaging signal, image reconstruction to generate a medical image.

* * * * *